United States Patent
John et al.

(10) Patent No.: US 11,549,852 B2
(45) Date of Patent: Jan. 10, 2023

(54) SAP FLOW SENSORS

(71) Applicant: Calvert Ventures LLC, Seattle, WA (US)

(72) Inventors: Pushpam Joseph Aji John, Seattle, WA (US); Kevin Xu, Los Angeles, CA (US)

(73) Assignee: CALVERT VENTURES LLC, Seattle, WA (US)

( * ) Notice: Subject to any disclaimer, the term of this patent is extended or adjusted under 35 U.S.C. 154(b) by 0 days.

(21) Appl. No.: 17/575,024

(22) Filed: Jan. 13, 2022

(65) Prior Publication Data

US 2022/0221348 A1    Jul. 14, 2022

Related U.S. Application Data

(60) Provisional application No. 63/136,781, filed on Jan. 13, 2021.

(51) Int. Cl.
| | | |
|---|---|---|
| *G01K 13/02* | (2021.01) | |
| *G01N 33/00* | (2006.01) | |
| *A01G 7/00* | (2006.01) | |
| *G01K 7/02* | (2021.01) | |
| *G01F 1/684* | (2006.01) | |

(52) U.S. Cl.
CPC ......... *G01K 13/026* (2021.01); *G01F 1/6847* (2013.01); *G01K 7/02* (2013.01); *G01N 33/0098* (2013.01); *A01G 7/00* (2013.01)

(58) Field of Classification Search
CPC ...... G01K 13/026; G01K 7/02; G01F 1/6847; G01N 33/0098; A01G 7/00
See application file for complete search history.

(56) References Cited

U.S. PATENT DOCUMENTS

| | | | | | |
|---|---|---|---|---|---|
| 4,817,427 | A | * | 4/1989 | Kitano | ............... G01F 1/6847 47/1.01 R |
| 5,269,183 | A | * | 12/1993 | Van Bavel | ............... G01F 1/68 73/204.22 |
| 5,337,604 | A | * | 8/1994 | Van Bavel | ......... G01N 33/0098 73/204.22 |

(Continued)

OTHER PUBLICATIONS

Bohl et al., "Sap Flow Meter", Jul. 19, 2021, https://github.com/OPEnSLab-OSU/OPEnS-Lab-Home/wiki/Sap-Flow-Meter, 10 pages.

(Continued)

*Primary Examiner* — Nathaniel T Woodward
*Assistant Examiner* — Philip L Cotey
(74) *Attorney, Agent, or Firm* — Dority & Manning, P.A.

(57) ABSTRACT

Exemplary sap flow sensors are provided. A sap flow sensor includes a substrate having a main body and at least two arms spaced apart from one another. The at least two arms extend from the main body. The sap flow sensor further includes a sap flow gauge that is disposed on the substrate. The sap flow gauge is configured to monitor a flow rate of sap through a stem of a plant. The sap flow gauge includes a heating element coupled to an arm of the at least two arms. The sap flow gauge further includes a first temperature sensor and a second temperature sensor disposed on opposite sides of the heating element. The first temperature sensor and the second temperature sensor each coupled to a neighboring arm of the at least two arms.

18 Claims, 5 Drawing Sheets

(56) References Cited

U.S. PATENT DOCUMENTS

| | | | | |
|---|---|---|---|---|
| 5,367,905 | A * | 11/1994 | Senock | G01F 1/68 |
| | | | | 73/204.22 |
| 5,481,090 | A * | 1/1996 | Senock | G01F 1/68 |
| | | | | 219/535 |
| 7,280,892 | B2 * | 10/2007 | Bavel | A01G 7/00 |
| | | | | 239/69 |
| 8,590,373 | B1 * | 11/2013 | Van Bavel | G01F 1/6847 |
| | | | | 73/204.23 |
| 10,827,691 | B2 * | 11/2020 | Korhonen | A01G 23/10 |
| 2017/0010296 | A1 * | 1/2017 | Shimokawa | A01G 7/00 |
| 2018/0027725 | A1 * | 2/2018 | Koutsorodi | A01C 21/005 |
| 2018/0172737 | A1 * | 6/2018 | Makinson | G01R 22/061 |
| 2019/0274259 | A1 * | 9/2019 | Shimokawa | A01G 7/00 |
| 2020/0081026 | A1 * | 3/2020 | Shimokawa | A01G 7/00 |
| 2021/0099522 | A1 * | 4/2021 | Chiocco | G08G 5/0034 |

OTHER PUBLICATIONS

Burgess et al., "An Improved Heat Pulse Method to Measure Low and Reverse Rates of Sap Flow in Woody Plants", Tree Physiology, 21.9, 2001, pp. 589-598.

Davis et al., "Sap Flow Sensors: Construction, Quality Control, and Comparison", Sensors (Basel), vol. 12, No. 1, Jan. 2012, pp. 954-971.

Opensourceov.org, Community-Driven Resources for Measuring Drought Tolerance in Plants.

Xu, "Sapflow Using the External Heat Ratio Method", Oct. 2019, https://dotmotelabs.com/BlogArticles/external-heat-ratio.html, 6 pages.

* cited by examiner

SAP FLOW SENSORS

PRIORITY STATEMENT

The present application claims priority to U.S. Provisional Patent Application Ser. No. 63/136,781, filed Jan. 13, 2021, which is incorporated by reference herein in its entirety.

FIELD

The present disclosure relates generally to sap flow sensors for monitoring the flow rate of sap through a portion of a plant (e.g., the stem of a plant) and, more particularly, to self-contained sap flow sensors having improved structural features that reduce sensor noise.

BACKGROUND

Sap flow measurement techniques have proven instrumental for studying plant responses to changing environmental conditions. For example, sap is the fluid (chiefly water with dissolved sugar and mineral salts) that circulates the vascular system of a plant. Thus, measuring rate of which the sap flows through the plant can give insight into the health of the plant (or strand of a plant), the water consumption and/or usage of the plant, and/or the plant's transpiration.

Sap flow has been studied by injecting heat into the stem of plants and/or trees. For example, a few known approaches for estimating sap flow by injecting heat include the heat pulse velocity method and the heat ratio method. Both methods utilize a sap flow gauge having a heating element and multiple temperature sensors. The heating element can be configured to periodically supply a fixed amount of heat to a stem of the plant or tree over a period of time (typically measured in seconds), and the multiple temperature sensors measure the temperature of the stem at two different locations. The difference in temperature at the two locations of the stem between a certain duration after the heat pulse is fired can be used to calculate the sap flow through the stem.

However, problems exist with known sap flow gauges that utilize heat injection for estimating sap flow. For example, many known sap flow gauges are invasive, such that they require the body of the plant to be pierced or punctured. For example, invasive sap flow gauges require both a heating probe and temperature probes to be inserted into the body of the plant, which results in permanent damage to the plant. In addition, invasive sap flow gauges can be difficult to install and cannot be easily repositioned or replaced.

As such, non-invasive sap flow gauges are often favored but can be less accurate than the invasive alternative due to increased sensor noise. For example, a typical non-invasive sap flow gauge includes a heating element and temperature sensors positioned next to one another on a common substrate. This arrangement can cause unwanted error in the temperature measurement of the temperature sensor due to conductive heat transfer through the common substrate.

Accordingly, an improved sap flow gauge that is capable of measuring and monitoring sap flow within one or more stems a plant, without causing invasive damage to the plant, is desired in the art. Additionally, a sap flow gauge that advantageously minimizes sensor noise caused by conductive heat transfer through a substrate is desired.

BRIEF DESCRIPTION

Aspects and advantages of the sap flow sensors in accordance with the present disclosure will be set forth in part in the following description, or may be obvious from the description, or may be learned through practice of the technology.

In accordance with one embodiment, a sap flow sensor is provided. The sap flow sensor includes a substrate having a main body and at least two arms spaced apart from one another. The at least two arms extend from the main body. The sap flow sensor further includes a sap flow gauge that is disposed on the substrate. The sap flow gauge is configured to monitor a flow rate of sap through a portion of a plant. The sap flow gauge includes a heating element coupled to a first arm of the at least two arms. The sap flow gauge further includes a first temperature sensor and a second temperature sensor disposed on opposite sides of the heating element. The first temperature sensor and the second temperature sensor each coupled to a neighboring arm of the at least two arms.

In accordance with another embodiment, a sap flow sensor is provided. The sap flow sensor includes a unitary substrate composed of one or more printed circuit boards physically affixed to one another. The sap flow sensor further includes a sap flow gauge coupled to the one or more printed circuit boards. The sap flow gauge is configured to monitor a flow rate of sap through a portion of a plant by coupling to an exterior of the portion of the plant. One or more processors coupled to the one or more printed circuit boards and in operable communication with the sap flow gauge. The sap flow sensor further includes a memory coupled to the one or more printed circuit boards and in operable communication with the one or more processors.

In accordance with another embodiment, a computing system for monitoring plants is provided. The computing system includes a plurality of sap flow sensors. Each sap flow sensor includes: a sap flow gauge, the sap flow gauge configured to monitor a flow rate of sap through a portion of a plant by coupling to an exterior of the portion of the plant; one or more processors in operable communication with the sap flow gauge; a memory in operable communication with the one or more processors; and a network interface in operable communication with the one or more processors and operable to communicate using a wireless network protocol. The plurality of sap flow sensors are configured to operate in a mesh communications network wherein each of the sap flow sensors wirelessly communicates with at least one other of the sap flow sensors to facilitate upload of sap flow information collected by each sap flow sensor to a central computing system.

These and other features, aspects and advantages of the present sap flow sensors will become better understood with reference to the following description and appended claims. The accompanying drawings, which are incorporated in and constitute a part of this specification, illustrate embodiments of the technology and, together with the description, serve to explain the principles of the technology.

BRIEF DESCRIPTION OF THE DRAWINGS

A full and enabling disclosure of the present sap flow sensors, including the best mode of making and using the present systems and methods, directed to one of ordinary skill in the art, is set forth in the specification, which makes reference to the appended figures, in which.

DETAILED DESCRIPTION

Reference now will be made in detail to embodiments of the present sap flow sensors, one or more examples of which are illustrated in the drawings. Each example is provided by way of explanation, rather than limitation of, the technology. In fact, it will be apparent to those skilled in the art that modifications and variations can be made in the present technology without departing from the scope or spirit of the claimed technology. For instance, features illustrated or described as part of one embodiment can be used with another embodiment to yield a still further embodiment. Thus, it is intended that the present disclosure covers such modifications and variations as come within the scope of the appended claims and their equivalents.

The detailed description uses numerical and letter designations to refer to features in the drawings. Like or similar designations in the drawings and description have been used to refer to like or similar parts of the invention. As used herein, the terms "first", "second", and "third" may be used interchangeably to distinguish one component from another and are not intended to signify location or importance of the individual components.

As used herein, the terms "upstream" (or "forward") and "downstream" (or "aft") refer to the relative direction with respect to fluid flow in a fluid pathway. For example, "upstream" refers to the direction from which the fluid flows, and "downstream" refers to the direction to which the fluid flows. Terms of approximation, such as "generally," "substantially," or "about" include values within ten percent greater or less than the stated value. When used in the context of an angle or direction, such terms include within ten degrees greater or less than the stated angle or direction. For example, "generally vertical" includes directions within ten degrees of vertical in any direction, e.g., clockwise or counter-clockwise.

In general, the present subject matter is directed to sap flow sensors, which include sap flow gauges configured to monitor (or measure) the flow rate of sap through a stem, branch, or other portion of a plant. Example plants on which the sap flow sensor described herein may be used includes, but is not limited to: corn, tomatoes, sunflower, cabbage, onion, or others. As understood by those of skill in the art, sap is the fluid, chiefly water with dissolved sugars and mineral salts, that circulates the vascular system of a plant. For example, the sap flow gauges described herein may advantageously measure the sap flow rate (e.g. in m/s or cm/hr) through the xylem of a plant (e.g. the vascular tissue of a plant that conducts sap upward from the roots).

In many implementations of the present design, the sap flow sensor may give valuable insights to both the transpiration of a plant and evapotranspiration, which can be valuable when determining plant health. For example, transpiration refers to the exhalation of water vapor from a plant, and evapotranspiration is the sum of transpiration and evaporation. As is understood by those of skill in the art, both transpiration and evapotranspiration is generally greatest during the day (e.g. during hours of intense sun exposure). As such, the sap flow sensors described hereinbelow advantageously give insight to the amount of water usage by a given plant throughout the day. Accordingly, in one example application, the sap flow sensor may be used for automatic irrigation control. For example, when the sap flow sensor detects that the sap flow rate has dropped below a predetermined threshold for a certain time of day, the irrigation system may automatically initiate and provide additional water to the plant. In addition, the sap flow sensor(s) may be used for surveying a crop (e.g. prior to the installation of an irrigation system), in order to determine which plants in the crop utilize more water throughout the day.

In another example application, the exemplary sap flow sensors described herein may be used for properly rationing water to an entire crop. As is understood, minimizing water usage can favorably reduce operating costs for farmers or may be a necessity of farming in water-constrained regions. Accordingly, the sap flow sensors may be installed on each plant in a crop, in order to determine exactly how much water is used by each plant in the crop throughout the day, thereby allowing water to be properly rationed (e.g. not used in excess) and distributed to each plant.

In yet another example implementation, the sap flow sensors described herein may be used for detecting plant stress (or relative health). For example, the sap flow rate (e.g. over a given period of time) of a given plant may be compared against a nominal value of that same plant species, in order to determine the plant's health and/or relative stress levels. These insights can be used for determining if the plant is getting enough nutrients from the soil, enough (or too much) sun exposure, and/or adequate water throughout the day.

Figures 1, 2:
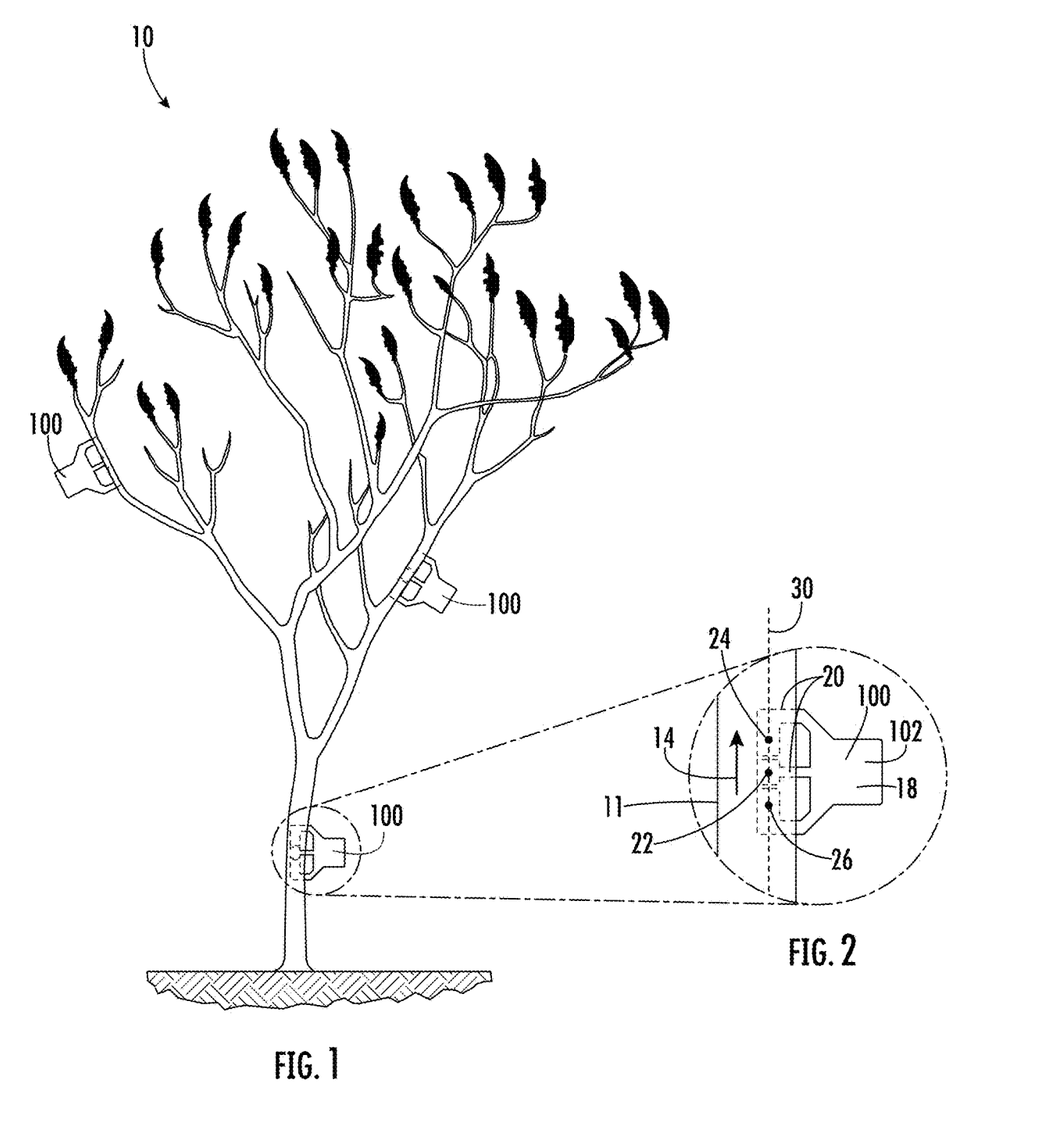
FIG. 1 is a schematic illustration of a plant having multiple sap flow sensors coupled thereto, in accordance with embodiments of the present disclosure.
FIG. 2 illustrates an enlarged view of one of the sap flow sensors shown in FIG. 1 attached to a stem of the plant, in accordance with embodiments of the present disclosure.

FIG. 1 illustrates a plant 10 having multiple sap flow sensors 100 coupled thereto. In particular, each of the sap flow sensors 100 may be coupled directly to an exterior surface 12 of the plant 10. For example, each of the sap flow sensors may be coupled to the plant 10 such that they only contact the exterior surface of the plant 10. In exemplary embodiments, as discussed below, each of the sap flow sensors 100 may be self-contained, singular, and cordless (e.g. a unitary, portable structure having a singular form factor). In this way, each of sap flow sensor 100 may couple directly to the exterior of the stem of a plant and be entirely cantilevered therefrom, such that the sap flow sensor is not tethered to other structures via any cords or wires as shown in FIG. 1. This feature may advantageously allow each of the sap flow sensors 100 to be easily moved, repositioned, or replaced without any wiring. For example, the sap flow sensor may only be physically coupled to the exterior 12 of the plant 10 stem during operation, such that no cords or wires extend from the sap flow sensor 100. In some of such embodiments, all of the data collected by the sap flow gauge may be wirelessly communicated (e.g. via a network interface) to a controller (e.g., implemented by a central computing system such as, for example, a cloud-based or on-premises server or other computing device). In other embodiments, the key sap flow metrics or data from the sap flow gauge may be aggregated on the sap flow sensor 100 itself, such that not all the data needs to be communicated.

FIG. 2 illustrates an enlarged view of a portion of the plant 10, to which a sap flow sensor 100 is attached. In particular, FIG. 2 illustrates a stem or petiole 11 of the plant 10 having a sap flow sensor 100 in accordance with the present invention attached thereto. The sap flow sensor 100 may be configured to measure the rate at which a flow of sap 14 passes through the stem 11. As shown in FIG. 2, the sap 14 generally flows from the ground, through the stems of the plant 10, to the shoots.

In particular embodiments, the sap flow sensor 100 may be composed of a substrate 102 having a main body 18 and one or more arms 20 that extend from the main body 18. In many embodiments, the one or more arms 20 may contact the exterior surface 12 of the plant 10 in operation of the sap flow sensor 100. In some embodiments, only the one or more arms 20 may contact the exterior surface 12 of the plant 10 in operation of the sap flow sensor 100, such that the main body 18 is cantilevered from the plant 10 and extends into the ambient environment (e.g. the air or atmosphere).

In various embodiments, the arms 20 and/or the main body 18 of the sap flow sensor 100 may be rigid (e.g. inflexible), thereby advantageously providing additional structural integrity and strength to the sap flow sensor 100. In such embodiments, the substrate 102 may be partially or entirely composed of a printed circuit board (PCB). For example, the printed circuit board may include layers of copper or other conductive material laminated onto and/or between sheet layers of a non-conductive substrate. Further, in such embodiments, the temperature sensors 24, 26 and/or the heating element 22 (as well as any other components) may be soldered onto the PCB to both electrically connect and mechanically fasten them to it. The PCBs described herein may be single-sided (one copper layer), double-sided (two copper layers on both sides of one substrate layer), or multi-layer (outer and inner layers of copper, alternating with layers of substrate). Multi-layer PCBs allow for much higher component density, because circuit traces on the inner layers would otherwise take up surface space between components.

In other embodiments, the arms 20 and/or the main body 18 of the sap flow sensor 100 may be malleable or flexible (e.g. compliant such that they can bend without breaking). In such embodiments, the arms 20 may bend or flex to correspond to the contour of the exterior surface 12 of the plant 10. Additionally, in such embodiments, the substrate 102 may be composed of a flexible printed circuit board. For example, the flexible printed circuit board may be a thin insulating polymer film having conductive circuit patterns affixed thereto, which, in some embodiments, may be supplied with a thin polymer coating to protect the conductor circuits. In embodiments utilizing a flexible printed circuit board, the substrate 102 (or portions of the substrate 102) may be non-rigid or compliant such that it can bend around a stem having a small diameter (e.g. 1 cm) without breaking.

As shown in FIG. 2, and described in more detail below, the sap flow sensor 100 may further include a heating element 22, a first temperature sensor 24, and a second temperature sensor 26 spaced apart from one another and disposed on the one or more arms 20. in the particular embodiment shown in FIG. 2, each of the heating element 22, the first temperature sensor 24, and the second temperature sensor 26 may be disposed on a respective arm 20 of the one or more arms 20 (such that the sensor 100 includes at least three arms in some embodiments). In other embodiments, as will be discussed, the sap flow sensor 100 may include only two arms, such that the temperature sensors 24, 26 are disposed on one arm, and the heating element 22 is disposed on another arm 20. Each of the temperature sensors 24 and 26 described herein may be any one of, but not limited to, the following: HDC2080, Thermocouple, Thermistor, RTD, or other suitable temperature measurement sensor.

In exemplary embodiments, the heating element 22, the first temperature sensor 24, and the second temperature sensor 26 may be mutually aligned along a common axis 30, which advantageously provides for increased accuracy when measuring a flow of sap 14. As shown in FIG. 2, the common axis 30 may be generally parallel to both the flow of sap 14 and the stem 11, which increases the accuracy of the sap flow measurement.

During operation of the sap flow sensor 100, the heating element transmits heat pulses to the stem 11 at a predetermined frequency (which can be adjusted by a user). The temperature sensors 24 and 26 may be spaced apart from the heating element 22 and may measure the temperature of the stem 11 on either side of the heating element 22. The temperature measurements may then be analyzed using a controller in order to determine the rate at which the flow of sap 14 is passing through the stem 11. In many embodiments, controller may utilize the heat ratio method (HRM) in order to calculate the heat pulse velocity ($V_h$) of the flow of sap 14. For example, in some implementations, the heat pulse velocity can be calculated according to the following equation:

$$V_h = \frac{k}{x} \ln\left(\frac{\Delta tc1}{\Delta tc2}\right)$$

Where $\Delta tc1$ is the downstream temperature difference between tc1 before the heat pulse is fired and after the heating pulse has subsided, similarly $\Delta tc2$ is the upstream temperature difference. x is the distance between the heating element and temperature sensors. k is the thermal diffusivity constant (units $cm^2/s$), and k may be obtained by the following equation:

$$k = \frac{x^2}{4 * t_m}$$

Where $t_m$ is time between heat pulse and maximum temperature rise under zero sap flow conditions. In many implementations, the heat pulse velocity ($V_h$) may be adjusted for the effect of non-hydroactive materials, including the gauge and bark, to sap velocity ($V_s$), which may be calculated according to the following equation:

$$V_s = V_h * m_{sap}$$

Where $m_{sap}$ is the constant that offsets effects of these materials on heat transfer.

In exemplary implementations, as shown in FIG. 1, multiple sap flow sensors 100 may be provided or installed onto a single plant 10, which advantageously provides spatial resolution. For example, the multiple sap flow sensors 100 may be positioned on different portions of the plant 10, in order to determine which portion of the plant is the healthiest and/or the least healthy. In some embodiments, the multiple sap flow sensors 100 may provide spatial resolution that can be used to detect diseased portions of the plant. In another example, sap flow measurements retrieved from multiple portions of the plant can be aggregated to generate a single sap flow measure for the plant which has improved accuracy due to readings coming from multiple different portions of the plant.

Figure 3:
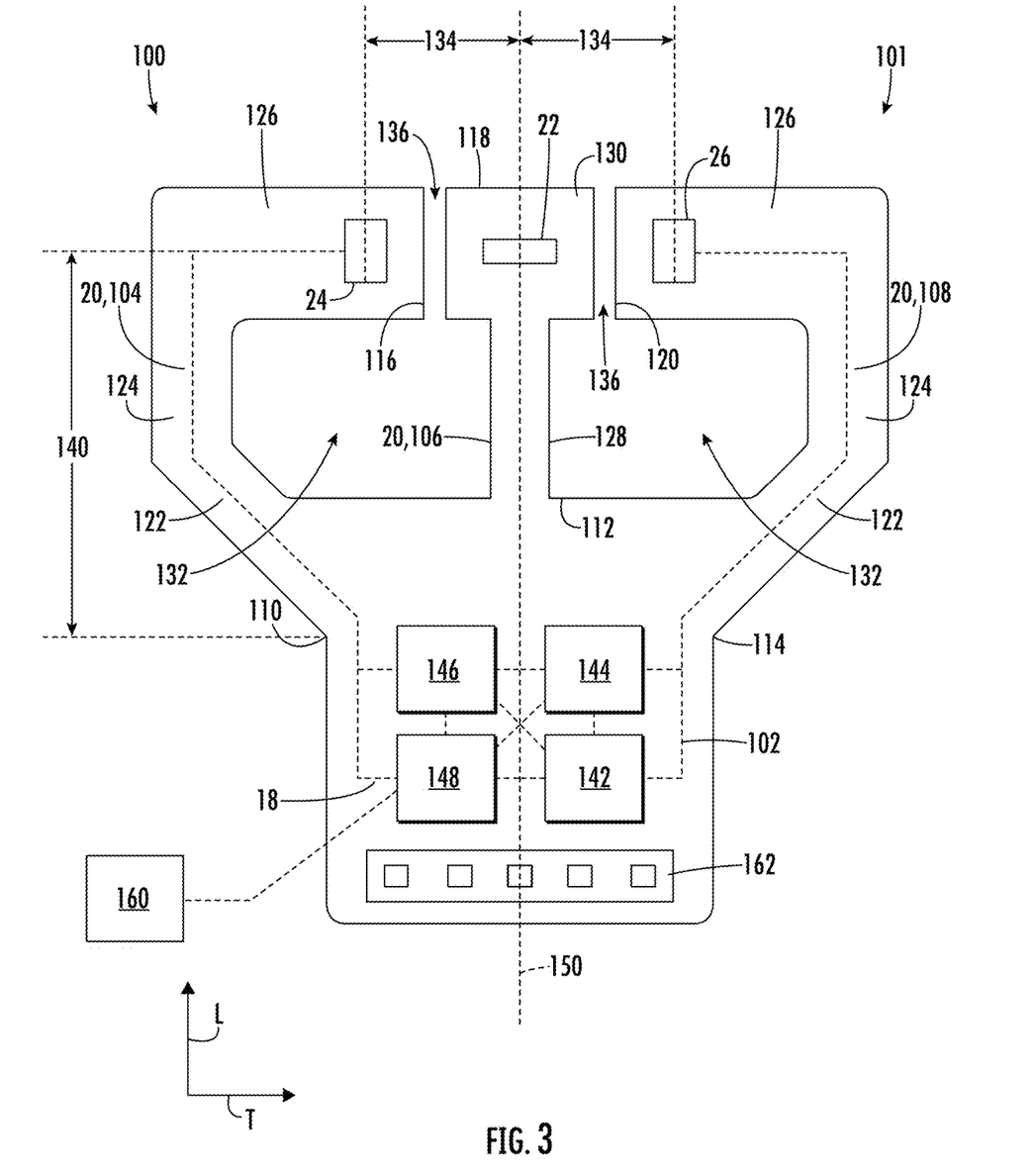
FIG. 3 illustrates a sap flow sensor, in accordance with embodiments of the present disclosure.

FIG. 3 illustrates a sap flow sensor 100 having a sap flow gauge 101, which is decoupled from a plant 10, in accordance with embodiments of the present disclosure. The sap flow sensor 100 may define a longitudinal axis L and a transverse axis T that are mutually perpendicular to one another. As used herein, the term "longitudinally" refers to the relative direction that is substantially parallel and/or coaxially aligned to a longitudinal centerline 150 of the sap flow sensor 100, and the term "transversely" may refer to the relative direction that is substantially perpendicular to the longitudinal centerline 150 of the sap flow sensor 100.

In many embodiments, the sap flow sensor 100 may include (e.g. be composed of) a substrate 102, and the sap flow gauge 101 may be disposed on the substrate 102. The substrate 102 may include a main body 18 and at least two arms 20, which are spaced apart from one another and each extend from the main body 18. In particular, the arms 20 may extend from the main body 18 of the substrate 102 such that they are cantilevered from the main body. In the embodiment shown in FIG. 3, the at least two arms 20 may include a first arm 104, a second arm 106, and a third arm 108. Each of the arms 104, 106, and 108 may extend from a respective connection point 110, 112, 114, at which each respective arm 104, 106, 108 is coupled to the main body, to a respective free end 116, 118, 120, at which each of the respective arms 104, 106, 108 terminates.

In particular embodiments, the first arm 104 and the third arm 108 of the sap flow sensor 100 may each include a diverging portion 122, a parallel portion 124, and a converging portion 126. Each diverging portion 122 may diverge away from the longitudinal centerline 150 as they extend from the respective connection point 110 to the respective parallel portion 124. Each parallel portion 124 may extend generally parallel to the longitudinal centerline 150 from the respective diverging portion 122 to the respective converging portion 126. Each converging portion 126 may converge towards the longitudinal centerline 150 as they extend from the respective parallel portion 124 to respective free end 116, 120.

The second arm 106 may be disposed transversely between the first arm 104 and the second arm 106. In particular embodiments, the second arm 106 may extend entirely along the longitudinal centerline 150 of the sap flow sensor 100 (e.g. entirely parallel to the longitudinal direction L). In many embodiments the second arm 106 may include a first portion 128 that extends from the connection point 112 to a second portion 130, and the first portion 128 may define a transverse width that is less than the transverse width of the second portion 130.

In many embodiments, as shown, the sap flow gauge 101 may include a heating element coupled to an arm 20 of the at least two arms 20. Additionally, the sap flow gauge 101 may include a first temperature sensor 24 and a second temperature sensor 26 disposed on opposite sides of the heating element 22 and each coupled to a neighboring arm 20 of the at least two arms 20. For example, in exemplary embodiments, the first temperature sensor 24 may be coupled to the first arm 104, the heating element 22 may be coupled to the second arm 106, and the second temperature sensor 24 may be coupled to the third arm 108. In particular embodiments, as shown, the first temperature sensor 24 may be coupled to the converging portion 126 of the first arm 104, and the second temperature sensor 26 may be coupled to the converging portion 126 of the third arm 108. Additionally, the heating element 22 may be positioned on the second portion 130 of the second arm 106 transversely between, and longitudinally aligned with, the first temperature sensor 24 and the second temperature sensor 26.

The spacing between the arms 104, 106, and 108 in the manner shown in FIG. 3 and described herein advantageously prevents the temperature sensors 24, 26 from picking up thermal noise that could otherwise conductively travel from the heating element 22 through the substrate 102. For example, the heating element and the temperature sensors 24, 26 being positioned on separate arms 20 and away from the main body 18 can advantageously reduce and/or entirely eliminate sensor error (or noise) that would otherwise be caused by conductive heat transfer through the substrate 102. In many embodiments, the arms 104, 106, 108 may collectively define openings 132 that advantageously reduce the area through which heat could travel on the substrate 102, thereby favorably reducing sensor noise in the temperature sensors 24 and 26.

In many embodiments, as shown the first temperature sensor 24 and the second temperature sensor 26 are disposed equidistant from the heating element 22. For example, the temperature sensors 24, 26 may be transversely spaced apart from the heating element 22 by a distance 134. In some embodiments, the distance 134 may be between about 0.1 centimeters and about 0.2 centimeters. In other embodiments, the distance 134 may be between about 0.1 centimeters and about 0.1 centimeters. In various embodiments, the distance 134 may be between about 0.4 centimeters and about 0.8 centimeters. In particular embodiments, the distance 134 may be between about 0.5 centimeters and about 0.7 centimeters. The distances 134 disclosed herein have been proven to optimize sensor performance while minimizing unwanted noise. In some implementations, the first temperature sensor 24 and the second temperature sensor 26 may be movable relative to the heating element 22, thereby permitting a user to adjust the distance 134.

In exemplary embodiments, the converging portions 126 of both the first arm 104 and the third arm 108 may be spaced apart from the second portion 130 of the second arm 106 such that a gap 136 is defined therebetween. These gaps 136 have been proven to advantageously reduce and/or entirely eliminate sensor error (or noise) that would otherwise be caused by conductive heat transfer through the substrate 102 between the heating element 22 and the temperature sensors 24, 26.

In many embodiments, the heating element 22, the first temperature sensor 24, and the second temperature sensor 26 may each be spaced apart from the main body 18 by a distance 140, which, in some embodiment, may be between about 0.1 centimeters and about 3 centimeters. In other embodiments, the distance 140 may be between about 0.2 centimeters and about 2 centimeters. In exemplary embodiments, the distance 140 may be between about 0.4 centimeters and about 0.8 centimeters. The distance 140 advantageously positioned the temperature sensors 24, 26 and the heating element 22 away from the main body 18, thereby allowing the main body to include on board power and computing elements (which could otherwise cause sensor error due to thermal noise).

In many embodiments, as shown, the sap flow sensor 100 may include an on-board power supply 142 physically affixed to the main body 18 of the substrate 102. The on-board power supply 142 may be operatively connected to the temperature sensors 24, 26 and the heating element 22. In some embodiments, the on-board power supply 142 can be an on-board battery, such as an on-board lithium-ion battery or other suitable battery. In other embodiments, the sap flow sensor 100 may not include a battery, such that the sap flow sensors may employ one or more energy harvesting techniques. In such embodiments, the sap flow sensor 100 may be powered by one or more solar panels. In various embodiments, the sap flow sensor 100 can also be electrically connectable (e.g., via a micro USB port or other electrical and/or data connection port) to a wall outlet or other source of utility power or other appropriately rated power. Plugging the sap flow sensor into a wall outlet can recharge the on-board battery.

In various implementations, as shown, the sap flow sensor 100 may include one or more processors 144 and a memory 146 coupled directly to the substrate 102 and in operable communication with the sap flow gauge 101, which advantageously allows the gauge 101 to collect and store sap flow data locally on the sap flow sensor 100. The one or more processors 144 and the memory 146 may be operatively connected to each of the temperature sensors 24, 26, the heating element 22, and the power source 142. The one or more processors 144 can be any suitable processing device (e.g., a processor core, a microprocessor, an ASIC, a FPGA, a controller, a microcontroller, etc.) and can be one processor or a plurality of processors that are operatively connected. The memory 146 can include one or more non-transitory computer-readable storage media, such as RAM, ROM, EEPROM, EPROM, one or more memory devices, flash memory devices, etc., and combinations thereof.

The memory 146 can store information that can be accessed by the one or more processors 144. For instance, the memory 146 (e.g., one or more non-transitory computer-readable storage mediums, memory devices) can store data (e.g. form the temperature sensors 24, 26) that can be obtained, received, accessed, written, manipulated, created, and/or stored. The memory 146 can also store computer-readable instructions that can be executed by the one or more processors 144. The instructions can be software written in any suitable programming language or can be implemented in hardware. Additionally, or alternatively, the instructions can be executed in logically and/or virtually separate threads on processor(s) 144. For example, the memory 146 can store instructions that when executed by the one or more processors 144 cause the one or more processors 144 to perform any of the operations and/or functions described herein.

The sap flow sensor 100 may further include a network interface 148 coupled to the substrate 102 (e.g. coupled directly to the main body of the substrate). The network interface 148 can include any number of components to provide networked communications (e.g., transceivers, antennas, controllers, cards, etc.). In some implementations, the network interface 148 may be operable to communicate using a wireless protocol, such as, for example, Wi-Fi, cellular, radio, Bluetooth and/or Bluetooth Low Energy. Further, the sensor 100 can be operable to communicate with a central computing device 160 using the wireless protocol. For example the central computing device 160 can be a user computing device (e.g., laptop) or other computing system (e.g., cloud-based or on-premises server system).

In some implementations, the sap flow sensor 100 communicatively connects to the central computing device 160 over via the network interface using the wireless protocol. In many implementations, the central computing device 160 can perform data curation and/or collection from the sap flow gauge 101. In particular, in some implementations, when connected to sap flow sensor 100, the computing device 160 can select certain data stored in the sap flow sensor 100 (e.g. in the memory 146) for transfer to the central computing device 160. In operation, the sap flow sensor 100 can communicatively connect to another sap flow sensor 100 (such that the sensors 100 form a mesh network with one another and are capable of communicating data between each other).

As one example, each sap flow sensor 100 can upload data such as sap flow readings to the central computing device 160 (e.g., wirelessly via a mesh network). In another example, data (e.g., software or firmware updates) can be downloaded to each sap flow sensor 100. As one example, in some implementations, each sap flow sensor 100 can store and implement a local on-device machine learning model. The machine learning model can generate inferences based on the raw sensor data collected by the gauge. For example, the inferences can be made in real time. The inferences can be uploaded to the central computing device 160 rather than the raw sensor data. Having an on-device machine learning model on the sensor 100 can therefore provide enhanced data ownership: the owner of the sensor 100 does not need to upload the raw data but can instead simply upload inferences generated from the raw data. In addition, having an on-device machine learning model on the sensor 100 can save network resources as the inferences are generally smaller in data size versus the raw data itself. In addition, having an on-device machine learning model on the sensor 100 can enable plant-specific or crop-specific learning to be performed on device. For example, one or more learning routines or algorithms can be performed over time as data is collected so that the on-device machine learning model is re-trained with the collected data to thereafter provide inferences which are more accurate and attuned to the particular dynamics of the plant or crop for which the sensors 100 are being deployed. In one example, updates to the on-device machine learning model can be downloaded to each sensor 100 (e.g., wirelessly via a mesh network) and applied to update the local model at the sensor 100. In some implementations, parameters such as heat duration (i.e. the duration of a heat pulse applied to the plant by the heating element) and/or heat ratio window may be machined learned via the machine learning model described herein, which may be advantageous because such parameters are likely to vary between plant species.

Directly coupling the computing components (e.g. 142, 144, 146, and 148) to the substrate 102 of the sap flow sensor 100 advantageously allows the sap flow sensor 100 to be self-contained, singular, portable, and cordless. Additionally or alternatively, one or more of the computing components (e.g. 142, 144, 146, and 148) may be disposed on a separate PCB, which may be electrically and physically coupled directly to the main body 18 via a pin bank 162 (thereby allowing the sap flow sensor 100 to remain cordless in such embodiments). Each of sap flow sensor 100 may couple directly to the exterior of the stem of a plant 10 and be entirely cantilevered therefrom, such that the sap flow sensor 100 is not tethered via any cords or wires as shown in FIG. 1. This feature may favorably allow each of the sap flow sensors 100 to be easily moved, repositioned, or replaced without any wiring. In such embodiments, all of the data collected by the sap flow gauge may be wirelessly communicated (e.g. via a network interface) to a central computing device 160.

Figure 4:
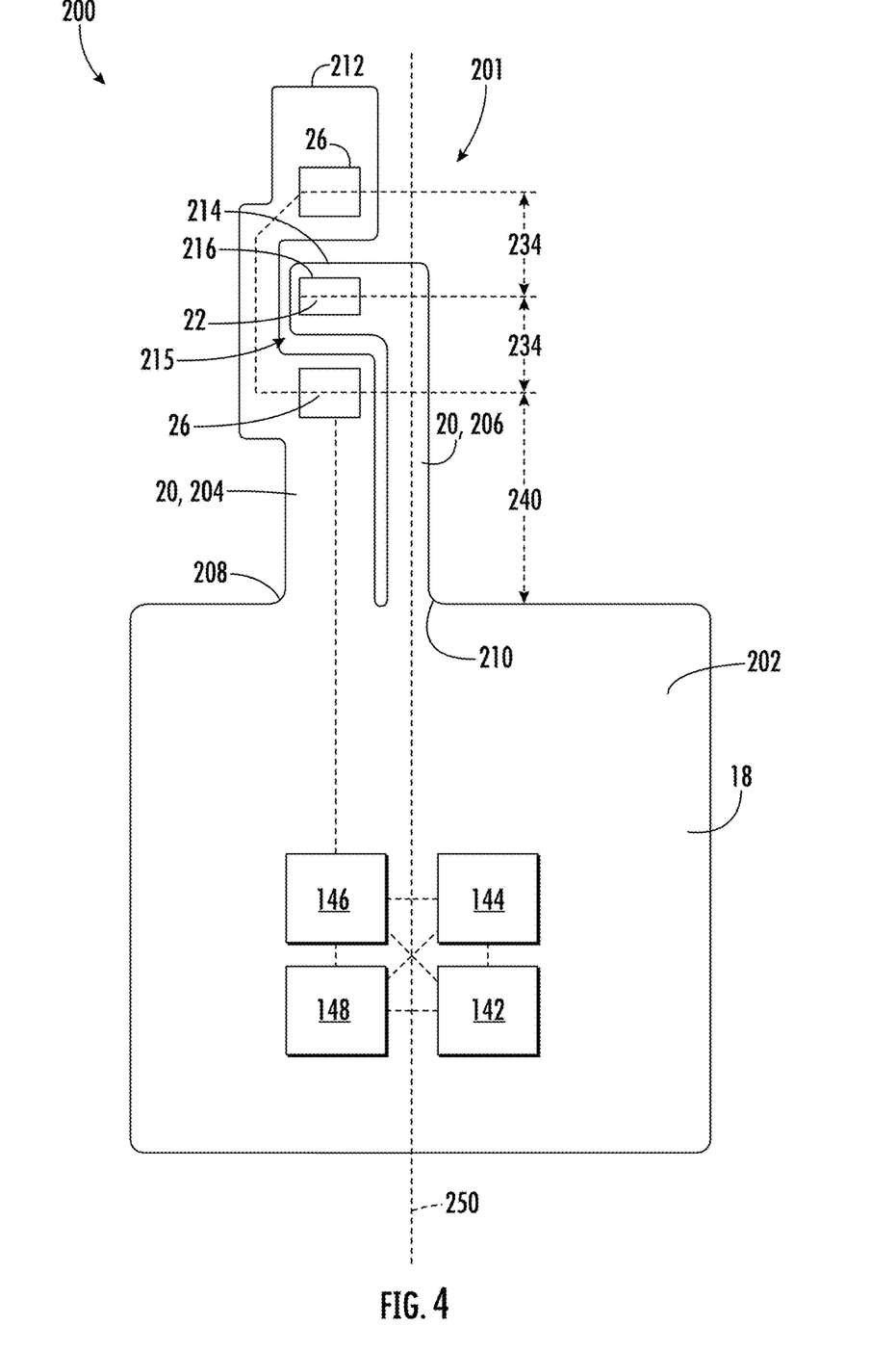
FIG. 4 illustrates an alternative embodiment of the sap flow sensor, in accordance with embodiments of the present disclosure.

FIG. 4 illustrates a sap flow sensor 200 having a sap flow gauge 201, which is decoupled from a plant 10, in accordance with an alternative embodiment of the present disclosure. The sap flow sensor 200 may define a longitudinal axis L and a transverse axis T that are mutually perpendicular to one another. As used herein, the term "longitudinally" refers to the relative direction that is substantially parallel and/or coaxially aligned to a longitudinal centerline 250 of the sap flow sensor 200, and the term "transversely" may refer to the relative direction that is substantially perpendicular to the longitudinal centerline 250 of the sap flow sensor 200.

In many embodiments, the sap flow sensor 200 may include (e.g. be composed of) a substrate 202, and the sap flow gauge 201 may be disposed on the substrate 202. The substrate 202 may include a main body 18 and at least two arms 20, which are spaced apart (e.g. transversely) from one another and each extend from the main body 18. In particular, the arms 20 may extend from the main body 18 of the substrate 202 such that they are cantilevered from the main body 18. In the embodiment shown in FIG. 4, the at least two arms 20 may include a first arm 204 and a second arm 206. The first arm 204 and the second arm 206 may extend from a respective connection point 208, 210, at which each respective arm 204, 206 is coupled to the main body 18, to a respective free end 212, 214, at which each of the respective arms 204, 206 terminates. In particular embodiments, the first arm 204 may define a notch 215 in the transverse direction T, and the second arm may include a transverse portion 216 that extends into the notch 215 but does not contact the first arm 204. In some embodiments, the second arm 206 may extend entirely along the longitudinal centerline 250 of the sap flow sensor 200 (e.g. entirely parallel to the longitudinal direction L).

In many embodiments, as shown, the sap flow sensor 200 may further include a sap flow gauge 201 having a heating element coupled to an arm 20 of the at least two arms 20. Additionally, the sap flow gauge 201 may include a first temperature sensor 24 and a second temperature sensor 26 disposed on opposite sides of the heating element 22 and each coupled to a neighboring arm 20 of the at least two arms 20. For example, in exemplary embodiments, the first temperature sensor 24 and the second temperature sensor may be coupled to the first arm 204 on opposite sides (e.g. opposite longitudinal sides) of the heating element 22. The heating element 22 may be coupled to the second arm 206, particularly coupled to the transverse portion 216 of the second arm 206 between the temperature sensors 24 and 26.

The spacing between the arms 204, 206 in the manner shown in FIG. 4 and described herein advantageously prevents the temperature sensors 24, 26 from picking up thermal noise that could otherwise conductively travel from the heating element 22 through the substrate 202 to the temperature sensor 24 or 26. For example, the heating element 22 and the temperature sensors 24, 26 being positioned on separate arms 20 and away from the main body 18 advantageously reduces and/or entirely eliminates sensor error (or noise) that would otherwise be caused by conductive heat transfer through the substrate 102.

In many embodiments, as shown the first temperature sensor 24 and the second temperature sensor 26 are disposed equidistant from the heating element 22. For example, the temperature sensors 24, 26 may be longitudinally spaced apart from the heating element 22 by a distance 234. In some embodiments, the distance 234 may be between about 0.1 centimeters and about 0.2 centimeters. In other embodiments, the distance 234 may be between about 0.1 centimeters and about 0.1 centimeters. In various embodiments, the distance 234 may be between about 0.4 centimeters and about 0.8 centimeters. In particular embodiments, the distance 234 may be between about 0.5 centimeters and about 0.7 centimeters. The distances 234 disclosed herein have been proven to optimize sensor performance while minimizing unwanted noise.

In many embodiments, the heating element 22, the first temperature sensor 24, and the second temperature sensor 26 may each be spaced apart from the main body 18 by at least a distance 240. For example, the first temperature sensor 26 may be spaced apart by exactly the distance 240, and the heating element 22 and the second temperature sensor are spaced apart a greater distance. In some embodiments, the distance 240 may be between about 0.1 centimeters and about 3 centimeters. In other embodiments, the distance 240 may be between about 0.5 centimeters and about 2 centimeters. The distance 240 advantageously positioned the temperature sensors 24, 26 and the heating element 22 away from the main body 18, thereby allowing the main body 18 to include on board power and computing elements (which could otherwise cause sensor error due to thermal noise).

Figure 5:
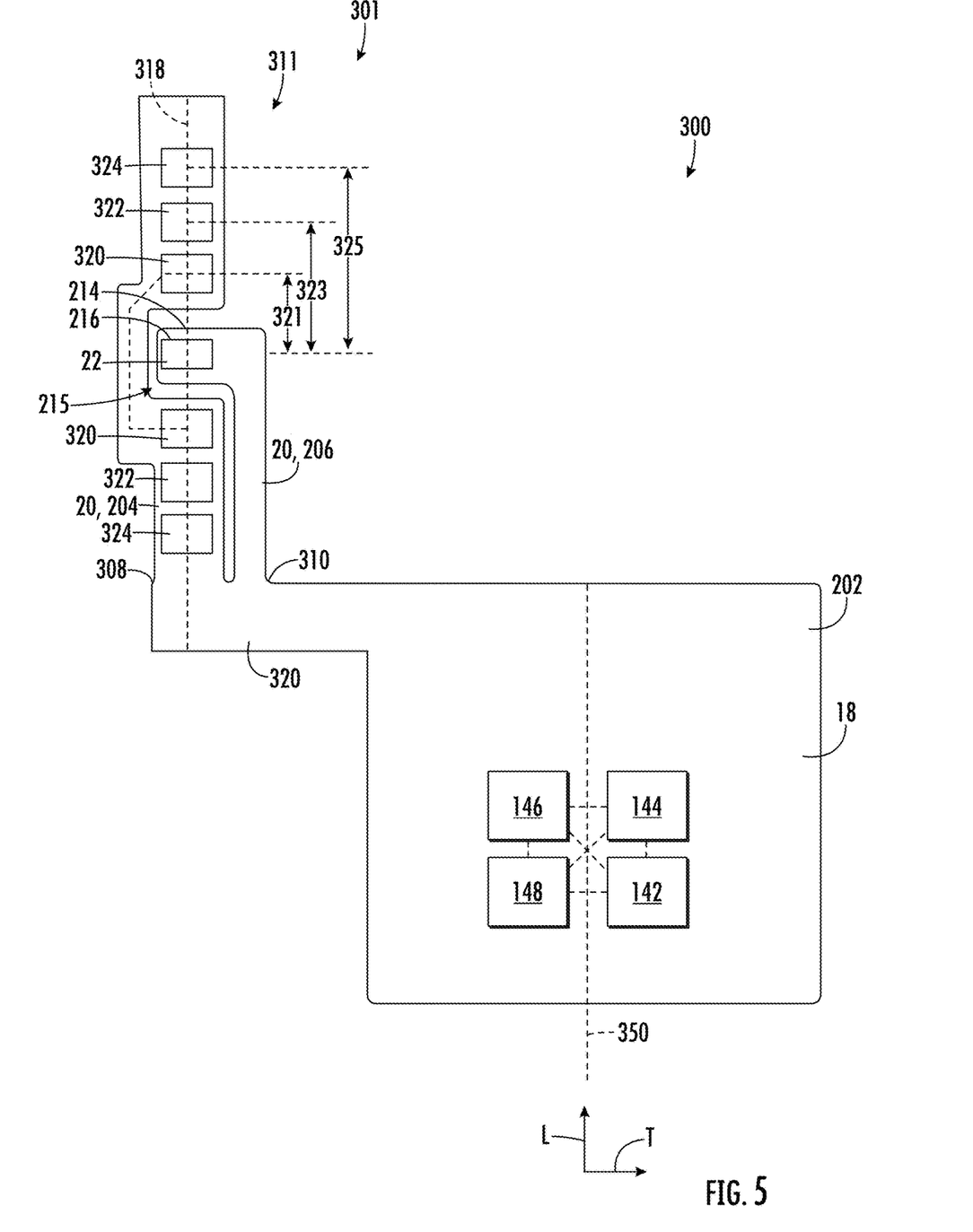
FIG. 5 illustrates an alternative embodiment of the sap flow sensor, in accordance with embodiments of the present disclosure.

FIG. 5 illustrates a sap flow sensor 300 having a sap flow gauge 301 that is offset from the main body 18 in the transverse direction T, in accordance with an alternative embodiment of the present disclosure. The sap flow sensor 300 may define a longitudinal axis L and a transverse axis T that are mutually perpendicular to one another. As used herein, the term "longitudinally" refers to the relative direction that is substantially parallel and/or coaxially aligned to a longitudinal centerline 350 of the sap flow sensor 300, and the term "transversely" may refer to the relative direction that is substantially perpendicular to the longitudinal centerline 350 of the sap flow sensor 300.

As shown, the sap flow sensor 300 may include a tab 302 extending transversely from the main body 202. This may advantageously increase the distance between the components disposed on the at least two arms 20 (e.g., the heating element 22 and the temperature sensors 24 and 26) and the components on the main body 18 (e.g., the power supply 142, the processors 144, memory 146, the network interface 148, and other components disposed on the main body 18). For example, the main body 18 may be shaped generally rectangularly, and the tab 302 may extend transversely from one of the corners of the main body 18. As shown in FIG. 5, the at least two arms 20 may extend directly from the tab 302. In particular, the arms 20 may extend generally longitudinally from the tab 302 such that they are cantilevered from the tab 302. The first arm 204 and the second arm 206 may extend (e.g., longitudinally) from a respective connection point 308, 310, at which each respective arm 204, 206 is coupled to the tab 302, to a respective free end 312, 314, at which each of the respective arms 204, 206 terminates. In this way, the arms 204, 206 may be offset from the main body 18 (and the longitudinal centerline 350) in the transverse direction T. Offsetting the at least two arms 20 in this manner has been proven to reduce sensor noise that could otherwise be caused by conductive heat transfer through the substrate 202.

In many embodiments, as shown, the sap flow sensor 300 may further include a sap flow gauge 301 having a heating element 22 and a plurality of temperature sensors 311. The plurality of temperature sensors 311 may be coupled to the first arm 204, and the heating element 22 may be coupled to the second arm 206. The heating element 22 and the plurality of temperature sensors 311 may be aligned with one another and disposed on a common longitudinal line 318 (which is transversely offset from the longitudinal centerline 350). In exemplary embodiments, the plurality of temperature sensors 311 may include a first pair of temperature sensors 320, a second pair of temperature sensors 322, and a third pair of temperature sensors 324. The processors 144 may selectively collect data (which may be stored in the memory 146) from one or more of the first pair of temperature sensors 320, the second pair of temperature sensors 322, and/or the third pair of temperature sensors 324.

As shown in FIG. 5, each temperature sensor in the first pair of temperature sensors 320 may be spaced apart from the heating element 22 by a first distance 321. Each temperature sensor in the second pair of temperature sensors 322 may be spaced apart from the heating element 22 by a second distance 323. Each temperature sensor in the third pair of temperature sensors 324 may be spaced apart from the heating element 22 by a third distance 325. The third distance 325 may be longer than the first distance 321 and the second distance 323. The second distance 323 may be longer than the first distance 321 and shorter than the third distance 325. The first distance 321 may be shorter than the second distance 323 and the third distance 325.

Including multiple pairs of variably spaced temperature sensors advantageously increases the modularity of the sap flow gauge 301. For example, the processor 144 may selectively collect data from one of the pairs of temperature sensors 320, 322, and/or 324 depending on the branch size, plant species, or other factors.

Figure 6:
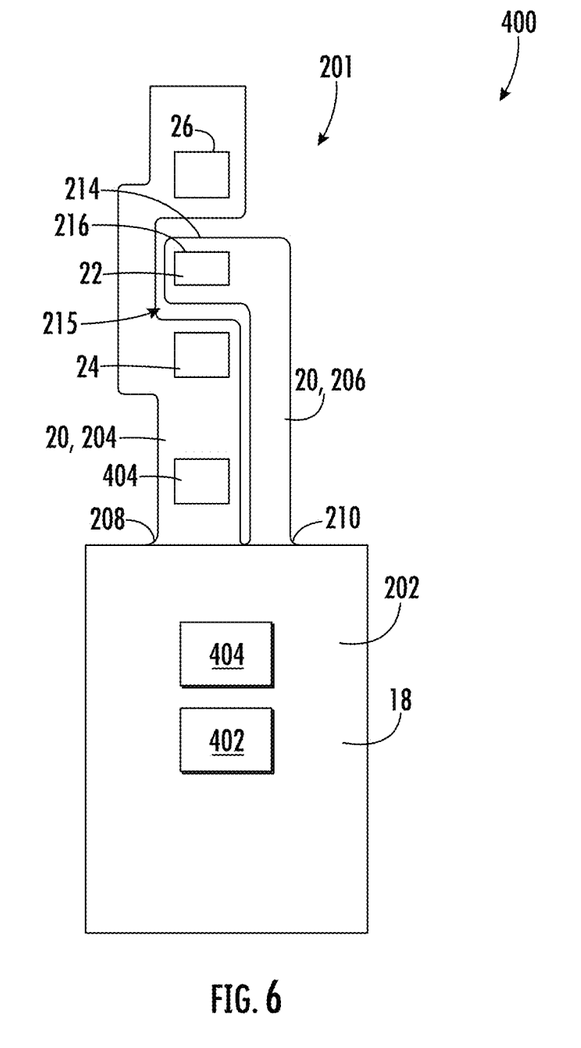
FIG. 6 illustrates an alternative embodiment of the sap flow sensor, in accordance with embodiments of the present disclosure.

FIG. 6 illustrates a sap flow sensor 400 having a sap flow gauge 201, in accordance with an alternative embodiment of the present disclosure. As shown, the sap flow sensor 400 may be a part of an "octopus" design, such that the sap flow sensor 400 is supported by a central sap flow sensor or unit (such as any one of the sap flow sensors 100, 200, or 300 described above with reference to FIGS. 3 through 5). In this way, the sap flow sensor 400 may not include an on-board processor, memory, or power supply. Instead, the sap flow sensor 400 may only include a network interface 402 coupled to the substrate 202 (e.g. coupled directly to the main body 18 of the substrate). The network interface 402 may be in operable communication with the network interface of a central unit or sap flow sensor (such as the network interface 148 of the sap flow sensors 100, 200, or 300 described above with reference to FIGS. 3 through 5).

The network interface 402 can include any number of components to provide networked communications (e.g., transceivers, antennas, controllers, cards, etc.). In some implementations, the network interface 402 may be operable to communicate using a wireless protocol, such as, for example, Wi-Fi, cellular, radio, Bluetooth and/or Bluetooth Low Energy. In some embodiments, the network interface 402, and/or the sap flow gauge 201, may be powered by an internal battery of the network interface 402. In some embodiments, as shown in FIG. 6, the sap flow sensor 400 may include one or more additional sensors 404. The one or more additional sensors 404 may be disposed on one or both of the main body 202 or an arm of the at least two arms 20. In various embodiments, the one or more additional sensors 404 may be a micro-electro-mechanical system (or MEMS sensor), an accelerometer, a magnetometer, and/or a gyroscope. In this way, the one or more additional sensors 404 may collect data indicative of a branch movement, wind speed, wind direction, and/or sensor orientation.

The sap flow sensors 200, 300, and 400 having only two arms 204, 206 as shown in FIGS. 4 through 6 may provide numerous advantages over sap flow sensors having more than two arms (such as three or more arms). For example, the sap flow sensors 200, 300, and 400 having only two arms 204, 206 may better secure to the branch or stem, may produce less rotational torque once secured, and may have reduced manufacturing costs relative to sap flow sensors having three or more arms.

In some example embodiments, an "octopus" configuration can include a plurality of sap flow sensors (e.g., the sap flow sensor 400 of FIG. 6) which are connected to a single central computing unit. For example, this configuration may allow a number of sap flow sensors to be positioned at various locations on a plant (e.g., see the multiple sensor positioned at various locations on a tree as shown in FIG. 1), while all connecting to a single central unit. Additionally or alternatively, this configuration may allow for a number of sap flow sensors to be positioned on multiple plants in a subsection of a plot, e.g., a group of citrus trees or corn plants in a plot. The sensors can be connected to the central unit in a wired or wireless fashion. In some example embodiments, a majority (e.g., all) of the computational components such as processors, memory, etc. can be contained in the central unit. This arrangement can enable the sap flow sensors to include fewer computational components (e.g., as described with respect to FIG. 6) and therefore to be relatively lighter in weight and therefore easier to attach to a plant.

The "octopus" configuration can also enable the central unit to receive and process and therefore gain/produce insights and intelligence from multiple sap flow sensors. As one example, the central unit can perform anomaly or error detection for the multiple sap flow sensors. For example, if readings from one sap flow sensor diverge significantly from readings from other sap flow sensors (e.g., other sap flow sensors at relatively similar locations) then the central unit can detect (e.g., and transmit or surface an alert) that an error or anomaly is occurring at the sensor.

In another example, the central unit can perform sensor fusion or other sensor processing techniques on sensor data (e.g., sap flow readings and/or accelerometer or other data) from the sensor(s). For example, a machine learning model or other algorithm can be trained and/or used to correct or refine sap flow sensor readings based on other sensor data (e.g., temperature data, accelerometer data, etc.). In another example, readings from a first sensor can be used to refine or correct readings from one or more second, different sensors. For example, a machine learning model or other algorithm can be trained and/or used to correct or refine sap flow sensor readings from the first sensor based on the data from the one or more second, different sensors.

In another example, readings from multiple sap flow sensors can provide a holistic view of the plant, which may enable the computing system to determine which part of the plant (or tree) is transpiring, stressed, and/or what type of ambient conditions it is experiencing. This also supports and/or provides data to validate when unusual sap flow data is recorded. For example, if a first sensor in the multiple sensors detects an unusual sap flow, then the other sensors in the multiple sap flow sensors may be used to contextualize, verify, and/or support the unusual sap flow data. This may be done to support temporal and spatial resolution of sap flow readings. For example, if plant performance data is desired at a specific time (or time period), then the sap flow sensors may each generate heat pulses and collect sap flow data separately in the minutes leading up to the specified time (e.g., the 15 minutes leading up). This sap flow data may be indicative of shade side (e.g., the orientation of the branch facing away from the sun), sun side (opposite the shade side), apex, under the stem for the specified time (or time period). This data may be integrated for the specified time, such that any subsequent data measured at a similar time may be compared to the historical data.

In another example, the central unit can enable power consumption savings by managing or controlling operations (e.g., operations that consume power such as activation of the heating element) of the multiple sensors in an intelligent fashion. As one example, the central unit can sequentially power on/off the sap flow sensors to obtain respective sap flow readings. By sequentially powering on/off the sap flow sensors to collect readings (e.g., as opposed to constantly powering the sensors and/or powering the sensors all at once) the total amount of power consumed can be reduced and/or the peak power consumed can be reduced, which may be beneficial when a power supply to the sensors is limited in total capacity and/or peak capacity (power output).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal language of the claims.

What is claimed is:

1. A sap flow sensor comprising:
   a substrate having a main body, a first arm extending from the main body, and a second arm extending from the main body and spaced apart from the first arm such that a gap is defined between the first arm and the second arm, wherein the first arm defines a notch, and wherein the second arm includes a transverse portion extending into the notch;
   a sap flow gauge disposed on the substrate, the sap flow gauge configured to monitor a flow rate of sap through a portion of a plant, the sap flow gauge comprising:
      a heating element coupled to the transverse portion of the second arm; and
      a first temperature sensor and a second temperature sensor disposed on opposite sides of the heating element and each coupled to the first arm.

2. The sap flow sensor as in claim 1, wherein the substrate is composed of one or more printed circuit boards.

3. The sap flow sensor as in claim 1, wherein the entire substrate is rigid.

4. The sap flow sensor as in claim 1, wherein the substrate is flexible.

5. The sap flow sensor as in claim 1, wherein the heating element, the first temperature sensor, and the second temperature sensor are mutually aligned along a common axis, the common axis extending across the gap.

6. The sap flow sensor as in claim 1, wherein the first temperature sensor and the second temperature sensor are disposed equidistant from the heating element.

7. The sap flow sensor as in claim 1, wherein the heating element, the first temperature sensor, and the second temperature sensor are each spaced apart from the main body by at least a distance of between about 0.1 centimeters and about 3 centimeters.

8. The sap flow sensor as in claim 1, wherein the sap flow gauge further comprises a third temperature sensor and a fourth temperature sensor disposed on the first arm on opposite sides of the heating element, wherein the first temperature sensor and the second temperature sensor are spaced apart from the heating element by a first distance, wherein the third temperature sensor and the fourth temperature sensor are spaced apart from the heating element by a second distance, and wherein the second distance is longer than the first distance.

9. The sap flow sensor as in claim 1, wherein a tab extends from a corner of the main body, and wherein the first arm and the second arm extend from the tab such that the first arm and the second arm are offset from a centerline of the main body of the substrate.

10. A sap flow sensor comprising:
    a unitary substrate composed of a printed circuit board, the unitary substrate having a main body, a first arm extending from the main body, and a second arm extending from the main body and spaced apart from the first arm such that a gap is defined between the first arm and the second arm, wherein the first arm defines a notch, and wherein the second arm includes a transverse portion extending into the notch;
    a sap flow gauge coupled to the printed circuit board, the sap flow gauge configured to monitor a flow rate of sap through a portion of a plant by coupling to an exterior of the portion of the plant, the sap flow gauge comprising a heating element coupled to the transverse portion of the second arm, the sap flow gauge further comprising a first temperature sensor and a second temperature sensor disposed on opposite sides of the heating element and each coupled to the first arm;
    one or more processors directly coupled to the printed circuit board and in operable communication with the sap flow gauge; and
    a memory directly coupled to the printed circuit board and in operable communication with the one or more processors.

11. The sap flow sensor as in claim 10, wherein the sap flow sensor is wireless.

12. The sap flow sensor as in claim 10, wherein the sap flow sensor further comprises a network interface coupled to the printed circuit board and operable to communicate using a wireless network protocol.

13. The sap flow sensor as in claim 12, wherein the wireless network protocol comprises one of radio-based communication, Wi-Fi, Bluetooth, or cellular.

14. The sap flow sensor as in claim 10, further comprising:
    a real time clock coupled to the printed circuit board and in operable communication with the one or more processors.

15. The sap flow sensor as in claim 10, wherein the first arm and the second arm each extend from a respective connection point at the main body to a respective free end.

16. The sap flow gauge as in claim 10, wherein the heating element, the first temperature sensor, and the second temperature sensor are mutually aligned along a common axis, wherein the common axis does not intersect the main body.

17. A computing system for monitoring plants, the computing system comprising:
    a plurality of sap flow sensors, wherein each sap flow sensor comprises:
    a substrate having a main body, a first arm extending from the main body, and a second arm extending from the main body and spaced apart from the first arm such that a gap is defined between the first arm and the second arm, wherein the first arm defines a notch, and wherein the second arm includes a transverse portion extending into the notch;
    a sap flow gauge, the sap flow gauge configured to monitor a flow rate of sap through a portion of a plant by coupling to an exterior of the portion of the plant, the sap flow gauge comprising a heating element coupled to the transverse portion of the second arm, the sap flow gauge further comprising a first temperature sensor and a second temperature sensor disposed on opposite sides of the heating element and each coupled to the first arm; and a network interface in operable communication with one or more processors and operable to communicate using a network protocol; and wherein the plurality of sap flow sensors are configured to communicate sap flow information to a central unit or at least one other of the sap flow sensors, and wherein each sap flow sensor is configured to store and implement a local on-device machine learning model, the machine learning model configured to generate inferences based on the sap flow data and upload the inferences to the central unit or one or more sap flow sensors of the plurality of sap flow sensors.

18. The computing system of claim 17, wherein the plurality of sap flow sensors are configured to operate in a mesh communications network wherein each of the sap flow sensors wirelessly communications with at least one other of the sap flow sensors to facilitate upload of the sap flow information collected by each sap flow sensor to a central computing system.

\* \* \* \* \*